United States Patent

Fukui et al.

Patent Number: 4,578,479
Date of Patent: Mar. 25, 1986

[54] PROCESS FOR PREPARING 1,2,4-TRIAZOLE-3-CARBOXAMIDES

[75] Inventors: Kiyoshi Fukui; Noboru Kakeya; Mitsushi Taguchi, all of Ichihara, Japan

[73] Assignee: Ube Industries, Ltd., Ube, Japan

[21] Appl. No.: 600,307

[22] Filed: Apr. 13, 1984

[30] Foreign Application Priority Data

Apr. 26, 1983 [JP] Japan .................................. 58-72066

[51] Int. Cl.$^4$ .................. C07D 249/14; C07D 401/06; C07D 403/06; C07D 413/06
[52] U.S. Cl. .................................. 548/269; 544/132; 544/366; 546/210; 548/518
[58] Field of Search ................ 548/269, 518; 546/210; 544/132, 366

[56] References Cited

FOREIGN PATENT DOCUMENTS 1512421  2/1968  France .............................. 548/269

OTHER PUBLICATIONS

Poonian et al.: Novel Precursor for Synthesis of C-Nucleoside Analogues of Ribavirin, J. Org. Chem. 45 (2) 1980, pp. 203–208.
Poonian et al.: A Total Synthesis of C-Nucleoside Analogues of Virazole, J. Org. Chem., vol. 42 (6) 1977, pp. 1109–1110.
Huynh-Dinh et al.: Synthesis of C-Nucleosides, Part 14 (1,2-4 Triazole Carboxamides) J. Chem. Soc. Perkin Trans I (7), 761–764, 1977.
Temple, Jr. et al.: Chem of Heterocyclic Cupds.—Triazoles 1,2,4: Carboxylic Acid and Deriv., pp. 96–97; 1981, John Wiley and Sons.
March: Advanced Organic Chem.: $R_x$, Mechanisms & Struct., 1977, 2nd Ed., pp. 914–917, 322–326.

Primary Examiner—Glennon H. Hollrah
Assistant Examiner—D. L. Dinner
Attorney, Agent, or Firm—Frishauf, Holtz, Goodman & Woodward

[57] ABSTRACT

There is disclosed a process for preparing a 1,2,4-triazole-3-carboxamide represented by the formula:

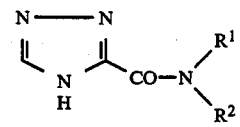

wherein, $R^1$ and $R^2$ represent independently a hydrogen atom, an alkyl group, a cycloalkyl group or an aryl group, or both $R^1$ and $R^2$ represent an alkylene group linked with each other directly or through an oxygen atom or a nitrogen atom to form a ring together with the nitrogen atom to which they are attached, which comprises subjecting an oxamohydrazide represented by the formula:

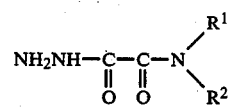

wherein $R^1$ and $R^2$ have the same meanings as defined above, to reaction with formamidine or a salt thereof.

15 Claims, No Drawings

PROCESS FOR PREPARING 1,2,4-TRIAZOLE-3-CARBOXAMIDES

This invention relates to a novel and simple process for preparing a 1,2,4-triazole-3-carboxamide conveniently.

In Latvijas PSR Zinatnu Akad. Vestis, Khim. Ser., (2), 204–208(1965), there is described obtaining 1,2,4-triazole-3-carboxamide starting from acetyl chloride through the six reaction steps described below:

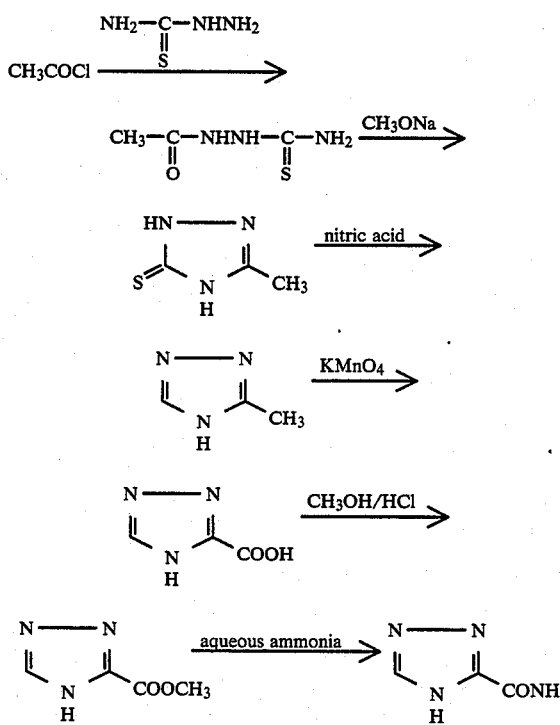

In Czechoslovakia Pat. No. 175,118, there is disclosed a process for preparing ethyl ester of 1,2,4-triazole-3-carboxylic acid, in which ethyl ester of thioxamide acid and formylhydrazine are subjected to reaction with each other at 50° to 60° C. to obtain ethyl (2-formylhydrazino)iminoacetate, which is then heated at 160° C. to form a closed ring by dehydration. Since ethyl ester of thioxamide acid can be synthesized by subjecting ethyl ester of oxamide acid, which is available from a reaction between ethyl oxalate and ammonia, to reaction with phosphorus pentasulfide, 1,2,4-triazole-3-carboxamide can be prepared from an oxalate through the five reaction steps described below.

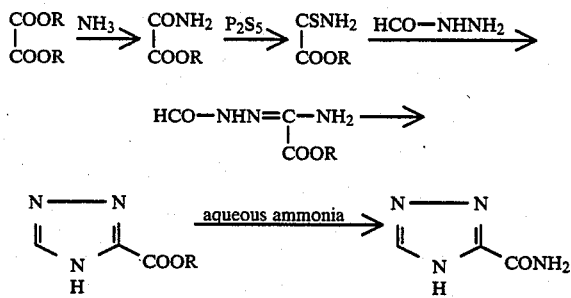

In this case, hydrogen sulfide is formed as a by-product and a complicated apparatus is required for deodorization thereof.

An object of this invention is to provide a novel process for preparing a 1,2,4-triazole-3-carboxamide.

Another object of this invention is to provide a process in which a 1,2,4-triazole-3-carboxamide is efficiently prepared without formation of by-products which require a complicated reaction apparatus for deodorization and the like.

This invention is a process for preparing a 1,2,4-triazole-3-carboxamide represented by the formula:

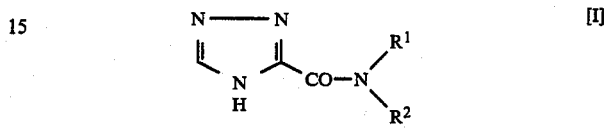

wherein, $R^1$ and $R^2$ represent independently a hydrogen atom, an alkyl group, a cycloalkyl group or an aryl group, or both $R^1$ and $R^2$ represent an alkylene group linked with each other directly or through an oxygen atom or a nitrogen atom to form a ring together with the nitrogen atom to which they are attached, which comprises subjecting an oxamohydrazide represented by the formula:

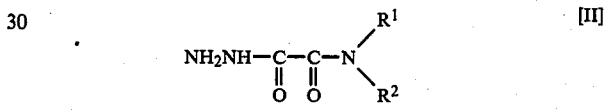

wherein $R^1$ and $R^2$ have the same meanings as defined above to reaction with formamidine or a salt thereof.

According to this invention, a 1,2,4-triazole-3-carboxamide can be obtained through a smaller number of reaction steps than those in the known processes and also without any use or by-production of ill-smelling compounds which have been used in the known processes.

As the examples of $R^1$ and $R^2$ in the above formula, there may be mentioned, in addition to a hydrogen atom; an alkyl group having 1–10 carbon atoms such as a methyl, ethyl, propyl, butyl, hexyl and benzyl groups; a cycloalkyl group having 5–7 carbon atoms such as a cyclopentyl, cyclohexyl and cycloheptyl groups; or an aryl group having 6–10 carbon atoms such as a phenyl group and a phenyl group substituted with an alkyl group having 1–4 carbon atoms or a halogen atom.

When $R^1$ and $R^2$ is linked, directly or through an oxygen atom or a nitrogen atom, to form a ring together with the nitrogen atom to which they are attached, they represent independently an alkylene group having 2–6 carbon atoms such as an ethylene, propylene, tetramethylene and pentamethylene groups.

The 1,2,4-triazole-3-carboxamide obtained according to the process of this invention are useful as an intermediate for ribavirin (Virazole) {see Ann. New York Acad. Sci., 284, 272–292 (1977)} which are antiviral agents.

The oxamohydrazide represented by the formula [I] can be obtained quantitatively by subjecting an ester of an oxamide acid, which is available from the reaction between an oxalate and an amine, to reaction with hydrazine by the following reaction steps.

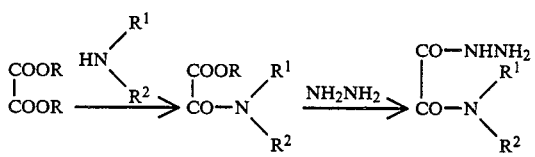

As the examples of the oxamohydrazide may be mentioned
oxamohydrazide,
N-methyloxamohydrazide,
N-ethyloxamohydrazide,
N-propyloxamohydrazide,
N-butyloxamohydrazide,
N-hexyloxamohydrazide,
N-benzyloxamohydrazide,
N-cyclopentyloxamohydrazide
N-cyclohexyloxamohydrazide,
N-phenyloxamohydrazide
N-tolyloxamohydrazide
N-chlorophenyloxamohydrazide
N-dichlorophenyloxamohydrazide
N-chlorotolyloxamohydrazide
N,N-dimethyloxamohydrazide,
N,N-diethyloxamohydrazide,
N,N-dipropyloxamohydrazide,
N,N-tetramethyleneoxamohydrazide
N,N-pentamethyleneoxamohydrazide
N,N-oxydiethyleneoxamohydrazide and
N,N-iminodiethyleneoxamohydrazide.

Salts of the formamidine include ones with a carboxylic acid such as formic acid, acetic acid and propionic acid; or ones with a mineral acid such as hydrochloric acid and sulfuric acid.

In order to obtain the desired product in good yield, the amount of the formamidine or their salts to be used may preferably be at least one mole relative to one mole of the oxamohydrazide.

The reaction may be carried out in the presence or absence of a solvent. The solvent to be used for the reaction includes alcohols such as methanol, ethanol, propanol and butanol; ethers such as ethylene glycol dimethyl ether and diethylene glycol dimethyl ether; amides such as formamide and N,N-dimethylformamide; pyridines such as pyridine, picoline and lutidine; and water.

Generally, there may be adopted a reaction temperature within the range of 20° to 200° C. While the reaction time may vary depending on the kinds of starting materials or the reaction temperature, the reaction may usually be completed within 2 to 3 hours when a reaction temperature of 100° C. or more is adopted.

The 1,2,4-triazole-3-carboxamide represented by the formula [I], which are formed by the above reaction, are in solid state at around ordinary temperature and can be isolated from the reaction mixture by means of a known isolating method, utilyzing the difference in solubilities of the components therein.

As the examples of the 1,2,4-triazole-3-carboxamide represented by the formula [I], there may be mentioned
1,2,4-triazole-3-carboxamide,
N-methyl-1,2,4-triazole-3-carboxamide,
N-ethyl-1,2,4-triazole-3-carboxamide,
N-propyl-1,2,4-triazole-3-carboxamide,
N-butyl-1,2,4-triazole-3-carboxamide,
N-hexyl-1,2,4-triazole-3-carboxamide,
N-benzyl-1,2,4-triazole-3-carboxamide,
N-cyclopentyl-1,2,4-triazole-3-carboxamide,
N-cyclohexyl-1,2,4-triazole-3-carboxamide,
N-phenyl-1,2,4-triazole-3-carboxamide
N-tolyl-1,2,4-triazole-3-carboxamide
N-chlorophenyl-1,2,4-triazole-3-carboxamide
N-dichlorophenyl-1,2,4-triazole-3-carboxamide
N-chlorotolyl-1,2,4-triazole-3-carboxamide
N,N-dimethyl-1,2,4-triazole-3-carboxamide,
N,N-diethyl-1,2,4-triazole-3-carboxamide
N,N-dipropyl-1,2,4-triazole-3-carboxamide
N,N-tetramethylene-1,2,4-triazole-3-carboxamide
N,N-pentamethylene-1,2,4-triazole-3-carboxamide
N,N-oxydiethylene-1,2,4-triazole-3-carboxamide and
N,N-iminodiethylene-1,2,4-triazole-3-carboxamide.

Examples of this invention are shown below. The yield of a 1,2,4-triazole-3-carboxamide in each Example is based on an oxamohydrazide used.

EXAMPLE 1

A mixture of 1.03 g of oxamohydrazide and 1.04 g of formamidine acetate was heated for reaction on an oil bath at 180° C. for one hour.

After the resulting reaction mixture was allowed to cool, 20 ml of 2-propanol was added thereto and the mixture was filtered. The thus obtained crystal was added to 30 ml of conc. aqueous ammonia and the mixture was stirred for 30 minutes at room temperature followed by filtration to obtain 0.25 g of oxamide as a crystal. The thus obtained filtrate free from oxamide was concentrated under reduced pressure to obtain 0.56 g (yield: 50%) of 1,2,4-triazole-3-carboxamide as a crystal, which was then recrystallized from 30 ml of water to obtain 0.43 g of a colorless needle-like crystal having a decomposition point of 316°–317° C. The results of elemental analysis are shown below.

|  | C | H | N |
| --- | --- | --- | --- |
| Found | 32.45 | 3.60 | 50.26 |
| Calculated (for $C_3H_4N_4O$) | 32.15 | 3.60 | 49.98 |

EXAMPLE 2

A mixture of 3.09 g of oxamohydrazide, 4.69 g of formamidine acetate and 60 ml of methanol was heated for reaction under reflux for 3 hours.

After reaction, the resulting reaction mixture was cooled to room temperature and then filtered. The thus obtained crystal was added to 150 ml of water containing 2.1 g of conc. aqueous ammonia. The resulting mixture was stirred for 30 minutes and then filtered to obtain 0.05 g of oxamohydrazide as a crystal. To the filtrate thus obtained was added 2.9 ml of conc. hydrochloric acid, followed by filtration to obtain 2.30 g (68%) of 1,2,4-triazole-3-carboxamide as a crystal.

EXAMPLE 3

A mixture of 3.09 g of oxamohydrazide, 3.63 g of formamidine hydrochloride and 70 ml of methanol was heated for reaction under reflux for 39 hours.

After reaction, the resulting reaction mixture was cooled to room temperature and then filtered. The thus obtained crystal was washed with 50 ml of water to obtain 2.55 g (76%) of 1,2,4-triazole-3-carboxamide as a crystal.

EXAMPLE 4

To a mixture of 3.09 g of oxamohydrazide and 100 ml of ethanol was added 4.69 g of formamidine acetate portionwise under reflux over 35 minutes. After addition of the salt, the reaction mixture was continously heated for reaction under reflux for 2 hours and 25 minutes. The reaction was carried out, while removing the solvent by distillation and supplying ethanol in an amount corresponding to that of the solvent thus removed.

After reaction, the resulting reaction mixture was cooled to room temperature and then filtered. The thus obtained crystal was added to a mixture of 10 ml of conc. aqueous ammonia and 40 ml of water. Then the mixture was stirred for one hour at room temperature and subsequently filtered to obtain 0.84 g of oxamohydrazide as a crystal. The filtrate was concentrated under reduced pressure to obtain 1.71 g (51%) of 1,2,4-triazole-3-carboxamide as a crystal.

EXAMPLE 5

After a mixture of 3.09 g of oxamohydrazide, 100 ml of ethanol and 60 ml of benzene was heated to remove 50 ml of the solvent by distillation under ambient pressure, 4.69 g of formamidine acetate was added portionwise to the reaction mixture under reflux over 20 minutes. After addition of the salt, the reaction mixture was reacted for further 26 hours by heating continuously under reflux. During the reaction, water formed was removed from the reaction system by azeotropic distillation.

After reaction, the resulting reaction mixture was cooled to room temperature and then filtered. The thus obtained crystal was added to a mixture of 50 ml of conc. aqueous ammonia and 100 ml of water, followed by filtration to obtain 0.26 g of oxamide as a crystal. The filtrate was concentrated under reduced pressure to obtain 2.36 g (70% of 1,2,4-triazole-3-carboxamide as a crystal.

EXAMPLE 6

A mixture of 3.09 g of oxamohydrazide, 4.69 g of formamidine acetate, 40 ml of ethanol and 40 ml of water was heated for reaction under reflux for one hour.

After reaction, the resulting reaction mixture was cooled to room temperature and then filtered. The thus obtained crystal was added to a mixture of 100 ml of conc. aqueous ammonia and 200 ml of water, followed by stirring at room temperature for 30 minutes and subsequent filtration to btain 0.18 g of oxamide as a crystal. The filtrate was concentrated under reduced pressure to obtain 2.24 g (67% of 1,2,4-triazole-3-carboxamide as a crystal.

EXAMPLE 7

A mixture of 1.03 g of oxamohydrazide, 1.04 g of formamidine acetate and 50 ml of 1-butanol was heated for reaction under reflux for one hour.

After reaction, the resulting reaction mixture was cooled to room temperature and then filtered. The thus obtained crystal was added to 30 ml of conc. aqueous ammonia, followed by filtration to obtain 0.17 g of oxamide as a crystal. The filtrate was concentrated under reduced pressure to obtain 0.69 g (62%) of 1,2,4-triazole-3-carboxamide as a crystal.

EXAMPLE 8

A mixture of 3.09 g of oxamohydrazide, 4.69 g of formamidine acetate and 60 ml of 1-butanol was heated for reaction under reflux for one hour.

After reaction, the resulting reaction mixture was cooled to room temperature and then filtered. The thus obtained crystal was added to a mixture of 2.1 g of conc. aqueous ammonia and 150 ml of water. The resulting reaction mixture was stirred at room temperature for one hour and then filtered to obtain 0.60 g of oxamide as a crystal. To the filtrate was added 3 ml of conc. hydrochloric acid, followed by filtration, to obtain 1.49 g (44%) of 1,2,4-triazole-3-carboxamide as a crystal.

EXAMPLE 9

A mixture of 1.03 g of oxamohydrazide, 1.04 g of formamidine acetate, 40 ml of 1-butanol and 10 ml of water was heated for reaction under reflux for one hour.

After reaction, the resulting reaction mixture was cooled to room temperature and then filtered to obtain 0.63 g (56%) of 1,2,4-triazole-3-carboxamide as a crystal.

EXAMPLE 10

A mixture of 1.03 g of oxamohydrazide, 1.04 g of formamidine acetate and 10 ml of diethylene glycol dimethyl ether was heated for reaction on an oil bath at 150° C. for one hour.

After reaction, the resulting reaction mixture was cooled to room temperature and then filtered. The thus obtained crystal was added to 30 ml of conc. aqueous ammonia, followed by stirring at room temperature for 30 minutes and subsequent filtration to obtain 0.22 g of oxamide as a crystal. The filtrate was concentrated under reduced pressure to obtain 0.51 g (46%) of 1,2,4-triazole-3-carboxamide as a crystal.

EXAMPLE 11

A mixture of 2.67 g of oxamohydrazide, 4.05 g of formamidine acetate and 30 ml of formamide was heated for reaction at 72° to 74° C. for 1.5 hours.

After reaction, the resulting reaction mixture was cooled to room temperature and then filtered. The thus obtained crystal was washed with 10 ml of 2-propanol and then added to a mixture of 20 ml of conc. aqueous ammonia and 80 ml of water. The resulting reaction mixture was stirred at room temperature for 10 minutes and then filtered to obtain 0.22 g of oxamide as a crystal. The filtrate was concentrated under reduced pressure to obtain 2.01 g (69%) of 1,2,4-triazole-3-carboxamide as a crystal.

EXAMPLE 12

A mixture of 3.09 g of oxamohydrazide, 3.12 g of formamidine acetate and 30 ml of formamide was heated for reaction at 116°-121° C. for one hour.

After reaction, the resulting reaction mixture was cooled to room temperature and then filtered. The thus obtained crystal was washed with 10 ml of 2-propanol and then added to 30 ml of conc. aqueous ammonia, followed by filtration, to obtain 0.27 g of oxamide as a crystal. The filtrate was concentrated under reduced pressure to obtain 2.45 g (73%) of 1,2,4-triazole-3-carboxamide as a crystal, which was then recrystallized from 150 ml of water to obtain 2.06 g of a crystal as a colorless needle.

EXAMPLE 13

A mixture of 1.03 g of oxamohydrazide, 1.04 g of formamidine acetate and 10 ml of formamide was heated for reaction on an oil bath at 150° C. for one hour.

After reaction, the resulting reaction mixture was cooled to room temperature and filtered. The thus obtained crystal was washed with 10 ml of 2-propanol and then added to 30 ml of conc. aqueous ammonia. The resulting reaction mixture was stirred at room temperature for 20 minutes and then filtered to obtain 0.11 g of oxamide as a crystal. The filtrate was concentrated under reduced pressure to obtain 0.83 g (74%) of 1,2,4-triazole-3-carboxamide as a crystal, which was then recrystallized from 40 ml of water to obtain 0.60 g of a crystal as a colorless needle. The results of elemental analysis are shown below.

|  | C | H | N |
|---|---|---|---|
| Found | 32.22 | 3.58 | 50.05 |
| Calculated (for $C_3H_4N_4O$) | 32.15 | 3.60 | 49.98 |

EXAMPLE 14

A mixture of 2.06 g of oxamohydrazide, 2.08 g of formamidine acetate and 20 ml of N,N-dimethylformamide was heated for reaction on an oil bath at 150° C. for one hour.

After reaction, the resulting reaction mixture was cooled to room temperature and then filtered. The thus obtained crystal was added to 50 ml of conc. aqueous ammonia, followed by filtration to obtain 0.33 g of oxamide as a crystal. The filtrate was concentrated under reduced pressure to obtain 0.90 g (40%) of 1,2,4-triazole-3-carboxamide as a crystal.

EXAMPLE 15

A mixture of 2.06 g of oxamohydrazide, 2.08 g of formamidine acetate and 50 ml of pyridine was heated for reaction under reflux for one hour.

After reaction, the resulting reaction mixture was cooled to room temperature and then filtered. The thus obtained crystal was washed with 60 ml of acetonitrile and then added to 50 ml of conc. aqueous ammonia, followed by filtration to obtain 0.50 g of oxamide as a crystal. The filtrate was concentrated under reduced pressure to obtain 1.15 g (51%) of 1,2,4-triazole-3-carboxamide as a crystal.

EXAMPLE 16

A mixture of 2.06 g of oxamohydrazide, 2.08 g of formamidine acetate and 100 ml of water was stirred for reaction at room temperature for 25 days.

After reaction, the resulting reaction mixture was filtered to obtain 0.86 g (38%) of 1,2,4-triazole-3-carboxamide as a crystal.

EXAMPLE 17

A mixture of 3.09 g of oxamohydrazide, 4.69 g of formamidine acetate and 60 ml of water was heated for reaction at 55°-57° C. for 3 hours.

After reaction, the resulting reaction mixture was cooled to room temperature and then filtered to obtain 1.89 g (56%) of 1,2,4-triazole-3-carboxamide as a crystal.

EXAMPLE 18

A mixture of 1.03 g of oxamohydrazide, 1.04 g of formamidine acetate and 50 ml of water was heated for reaction under reflux for one hour.

After reaction, the resulting reaction mixture was cooled to room temperature and then filtered to obtain 0.59 g (53%) of 1,2,4-triazole-3-carboxamide as a crystal.

EXAMPLE 19

To a mixture of 3.09 g of oxamohydrazide and 50 ml of water was added dropwise 20 ml of an aqueous solution containing 3.12 g of formamidine acetate over 53 minutes under reflux. After dropwise addition, the resulting reaction mixture was heated for reaction continuously for further 67 minutes.

After reaction, the thus obtained reaction mixture was cooled to room temperature and then filtered to obtain 1.76 g (52%) of 1,2,4-triazole-3-carboxamide as a crystal.

EXAMPLE 20

A mixture of 10.31 g of oxamohydrazide, 15.62 g of formamidine acetate and 200 ml of water was heated for reaction under reflux for 30 minutes.

After reaction, the resulting reaction mixture was cooled to room temperature and then filtered to obtain 8.30 g (74%) of 1,2,4-triazole-3-carboxamide as a crystal.

EXAMPLE 21

A mixture of 3.09 g of oxamohydrazide, 6.25 g of formamidine acetate and 70 ml of water was heated for reaction under reflux for 30 minutes.

After reaction, the resulting reaction mixture was cooled to room temperature and then filtered to obtain 2.54 g (76%) of 1,2,4-triazole-3-carboxamide as a crystal.

EXAMPLE 22

To 50 ml of an aqueous solution containing 15.62 g of formamidine hydrochloride was added 150 ml of a 1N aqueous sodium hydroxide solution under ice-cooling. To the resulting solution was added 10.31 g of oxamohydrazide and then the thus obtained mixture was heated for reaction under reflux for 30 minutes.

After reaction, the resulting reaction mixture was cooled to room temperature and then filtered to obtain 1.22 g (11%) of 1,2,4-triazole-3-carboxamide as a crystal. To the filtrate was added 70 ml of 1N hydrochloric acid, followed by filtration to obtain further 2.51 g (22%) of 1,2,4-triazole-3-carboxamide as a crystal.

EXAMPLE 23

A mixture of 3.09 g of oxamohydrazide, 2.42 g of formamidine hydrochloride and 70 ml of water was heated for reaction under reflux for 30 minutes.

After reaction, the resulting reaction mixture was cooled to room temperature and then filtered. The thus obtained crystal was added to a mixture of 4.80 g of conc. aqueous ammonia and 100 ml of water. The mixture thus obtained was stirred at room temperature for one hour and then filtered to obtain 0.52 g of oxamohydrazide as a crystal. To the filtrate was added 6.5 ml of conc. hydrochloric acid, followed by filtration to obtain 1.6 g (48%) of 1,2,4-triazole-3-carboxamide as a crystal.

EXAMPLE 24

A mixture of 3.09 g of oxamohydrazide, 3.63 g of formamidine hydrochloride and 70 ml of water was heated for reaction under reflux for 30 minutes.

After reaction, the resulting reaction mixture was cooled to room temperature and then filtered. The thus obtained crystal was added to a mixture of 5 g of conc. aqueous ammonia and 100 ml of water. The resulting mixture was stirred at room temperature for one hour and then filtered to remove the crystal of oxamohydrazide. To the filtrate was added 6.9 ml of conc. hydrochloric acid, followed by filtration to obtain 1.88 g (56%) of 1,2,4-triazole-3-carboxamide as a crystal.

EXAMPLE 25

A mixture of 5.86 g of N-methyloxamohydrazide, 6.25 g of formamidine acetate and 180 ml of 1-butanol was heated for reaction under reflux for 3 hours.

After reaction, the resulting reaction mixture was cooled to room temperature and then filtered to obtain 4.97 g (79%) of N-methyl-1,2,4-triazole-3-carboxamide as a crystal, which was then recrystallized from 2-propanol to obtain a colorless crystal having a decomposition point of 241°–242° C. The results of elemental analysis are shown below.

|  | C | H | N |
|---|---|---|---|
| Found | 38.33 | 4.94 | 44.18 |
| Calculated (for $C_4H_6N_4O$) | 38.04 | 4.80 | 44.42 |

EXAMPLE 26

A mixture of 3.58 g of N-phenyloxamohydrazide, 2.50 g of formamidine acetate and 70 ml of 1-butanol was heated for reaction under reflux for 3 hours.

After reaction, the resulting reaction mixture was cooled to room temperature and then filtered to obtain 2.85 g (76%) of N-phenyl-1,2,4-triazole-3-carboxamide as a crystal. The filtrate was concentrated under reduced pressure and to the thus obtained residue was added 20 ml of water, followed by filtration, to obtain further 0.7 g (19%) of N-phenyl-1,2,4-triazole-3-carboxamide as a crystal, which was then recrystallized from water to obtain a colorless crystal having a decomposition point of 228°–229.5° C. The results of elemental analysis are shown below.

|  | C | H | N |
|---|---|---|---|
| Found | 57.57 | 4.33 | 29.39 |
| Calculated (for $C_9H_8N_4O$) | 57.44 | 4.28 | 29.77 |

EXAMPLE 27

A mixture of 4.78 g of N,N-diethyloxamohydrazide, 3.13 g of formamidine acetate and 100 ml of 1-butanol was heated for reaction under reflux for 3 hours.

After reaction, the resulting reaction mixture was concentrated under reduced pressure. The residue thus obtained was recrystallized from 50 ml of benzene to obtain 0.98 g (19%) of N,N-diethyl-1,2,4-triazole-3-carboxamide as a colorless needle melting at 173°–174° C. The results of elemental analysis are shown below.

|  | C | H | N |
|---|---|---|---|
| Found | 49.59 | 7.18 | 33.64 |
| Calculated (for $C_7H_{12}N_4O$) | 49.99 | 7.19 | 33.31 |

We claim:

1. A process for preparing a 1,2,4-triazole-3-carboxamide represented by the formula:

$$\begin{array}{c} N\!\!-\!\!\!-\!\!\!-\!\!N \\ \| \quad \| \\ \diagdown_{N}\diagup^{CO-N}\diagdown_{R^2}^{R^1} \\ H \end{array}$$

wherein, $R^1$ and $R^2$ represent independently a hydrogen atom, an alkyl group having 1 to 10 carbon atoms, a cycloalkyl group having 5 to 7 carbon atoms or an aryl group having 6 to 10 carbon atoms or both $R^1$ and $R^2$ represent an alkylene group having 2 to 6 carbon atoms linked with each other directly or through an oxygen atom or a nitrogen atom to form a ring together with the nitrogen atom to which they are attached, which comprises subjecting an oxamohydrazide represented by the formula:

$$H_2N-NH-\underset{\underset{O}{\|}}{C}-\underset{\underset{O}{\|}}{C}-N\diagdown_{R^2}^{R^1}$$

wherein $R^1$ and $R^2$ have the same meanings as defined above,
to reaction with a water soluble salt of formamidine.

2. The process according to claim 1, wherein the reaction is carried out in the absence of a solvent.

3. The process according to claim 1, wherein the reaction is carried out in the presence of a solvent selected from the group consisting of methanol, ethanol, propanol, butanol, ethylene glycol dimethyl ether, diethylene glycol dimethyl ether, formamide, N,N-dimethylformamide, pyridine, picoline, lutidine and water.

4. The process according to claim 1, wherein the reaction is carried out at a temperature of 20° to 200° C.

5. The process according to claim 5, wherein the reaction is carried out at a temperature of 50° to 180° C.

6. The process according to claim 1, wherein the formamidine salt is used in an amount of at least one mole relative to one mole of the oxamohydrazide used.

7. The process according to claim 6, wherein the formamidine salt is used in an amount of 1 to 2 moles relative to one mole of the oxamohydrazide used.

8. The process according to claim 1, wherein at least one of $R^1$ and $R^2$ is an aryl group selected from the group consisting of phenyl, phenyl substituted with an alkyl group having 1 to 4 carbon atoms and phenyl substituted with halogen.

9. The process according to claim 1, wherein said oxamohydrazide is selected from the group consisting of
oxamohydrazide,
N-methyloxamohydrazide,
N-ethyloxamohydrazide,
N-propyloxamohydrazide,
N-butyloxamohydrazide, N-hexyloxamohydrazide,
N-benzyloxamohydrazide,
N-cyclopentyloxamohydrazide
N-cyclohexyloxamohydrazide,
N-phenyloxamohydrazide
N-tolyloxamohydrazide
N-chlorophenyloxamohydrazide
N-dichlorophenyloxamohydrazide
N-chlorotolyloxamohydrazide
N,N-dimethyloxamohydrazide,
N,N-diethyloxamohydrazide,
N,N-dipropyloxamohydrazide,
N,N-tetramethyleneoxamohydrazide
N,N-pentamethyleneoxamohydrazide
N,N-oxydiethyleneoxamohydrazide and
N,N-iminodiethyleneoxamohydrazide,
and said reaction is with a formamidine salt selected from the group consisting of salts of a carboxylic acid and a mineral acid wherein said carboxylic acid is formic acid, acetic acid or propionic acid and said mineral acid is hydrochloric acid or sulfuric acid.

10. The process according to claim 9, wherein said oxamohydrazide is oxamohydrazide.

11. The process according to claim 9, wherein said oxamohydrazide is N-methyloxamohydrazide.

12. The process according to claim 9, wherein said oxamohydrazide is N-phenyloxamohydrazide.

13. The process according to claim 9, wherein said oxamohydrazide is N-N-diethyloxamohydrazide.

14. The process according to claim 9, wherein said reaction is with the acetic acid salt of formamidine.

15. The process according to claim 9, wherein said reaction is with the hydrochloric acid salt of formamidine.

* * * * *